(12) United States Patent
Urizzi et al.

(10) Patent No.: US 11,395,685 B2
(45) Date of Patent: Jul. 26, 2022

(54) ORTHOPEDIC KIT

(71) Applicants: Andrea Urizzi, San Michele al Tagliamento (IT); Diego Risato, Vigo di Cadore (IT)

(72) Inventors: Andrea Urizzi, San Michele al Tagliamento (IT); Diego Risato, Vigo di Cadore (IT)

(*) Notice: Subject to any disclaimer, the term of this patent is extended or adjusted under 35 U.S.C. 154(b) by 0 days.

(21) Appl. No.: 17/252,235

(22) PCT Filed: Jul. 1, 2019

(86) PCT No.: PCT/IB2019/055597
§ 371 (c)(1),
(2) Date: Dec. 14, 2020

(87) PCT Pub. No.: WO2020/008335
PCT Pub. Date: Jan. 9, 2020

(65) Prior Publication Data
US 2021/0186581 A1 Jun. 24, 2021

(30) Foreign Application Priority Data
Jul. 3, 2018 (IT) .......... 102018000006879

(51) Int. Cl.
*A61B 17/80* (2006.01)
*A61B 17/88* (2006.01)
*A61B 17/17* (2006.01)

(52) U.S. Cl.
CPC ...... *A61B 17/8019* (2013.01); *A61B 17/1728* (2013.01); *A61B 17/808* (2013.01);
(Continued)

(58) Field of Classification Search
CPC ..... A61B 17/1728; A61B 17/66; A61B 17/80; A61B 17/8004; A61B 17/808;
(Continued)

(56) References Cited

U.S. PATENT DOCUMENTS 5,375,956 A * 12/1994 Pennig ............... A61B 17/8605
411/389
7,104,991 B2 * 9/2006 Dixon ................. A61B 17/1728
606/279

(Continued)

FOREIGN PATENT DOCUMENTS

CH 675531 A5 * 10/1990 ......... A61B 17/8052
CH 675531 * 12/2021
FR 2820631 8/2002

*Primary Examiner* — Larry E Waggle, Jr.
(74) *Attorney, Agent, or Firm* — Carmel Patent Agency; Robert Ballarini

(57) ABSTRACT

A kit for orthopedics, preferably for osteosynthesis, has a mechanical fixing system that includes a plate for straddling between two bone fragments and fixing screws for fixing the plate to the two bone fragments. The plate has a thickness of about 0.5-4 mm and conical through holes, the fixing screws each having a head, a self-tapping stem, and a conical collar interposed between the head and the self-tapping stem to define a conical coupling within a corresponding conical through hole of the plate. The heads of the fixing screws have a upper surfaces with a recessed and shaped mark for coupling with the tip of a screwing tool and external side walls with a thread for engaging a gripping tool. When the conical collar is inserted into a corresponding conical through hole of the plate, the head protrudes outwardly from the plate.

10 Claims, 8 Drawing Sheets

Figure 1:
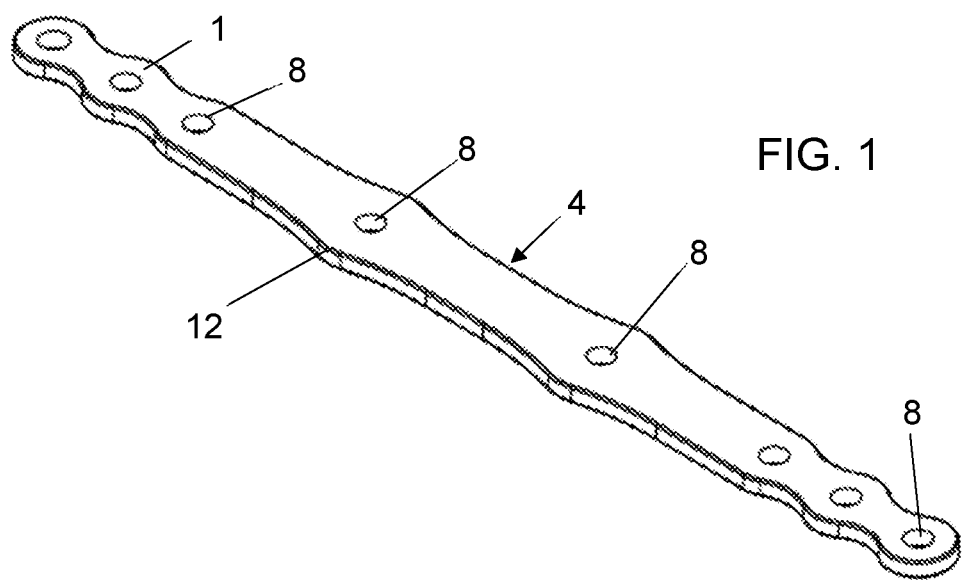

(52) U.S. Cl.
CPC ........ *A61B 17/8052* (2013.01); *A61B 17/888* (2013.01); *A61B 17/8891* (2013.01)

(58) Field of Classification Search
CPC ............ A61B 17/8019; A61B 17/8052; A61B 17/861; A61B 17/88; A61B 17/8875; A61B 17/888; A61B 17/8883; A61B 17/8886; A61B 17/8888; A61B 17/8891
See application file for complete search history.

(56) References Cited

U.S. PATENT DOCUMENTS

| | | | |
|---|---|---|---|
| 9,271,769 B2 * | 3/2016 | Batsch | ............... A61B 17/8057 |
| 9,867,639 B2 * | 1/2018 | Biedermann | ...... A61B 17/7059 |
| 10,426,535 B2 * | 10/2019 | Zander | ................. A61B 17/862 |
| 10,617,449 B2 * | 4/2020 | Corbin | ............... A61B 17/7077 |
| 2006/0089648 A1 | 4/2006 | Masini | |
| 2010/0130983 A1 * | 5/2010 | Thornhill | ........... A61B 17/1728 |
| | | | 606/96 |
| 2015/0216573 A1 | 8/2015 | Chin | |

* cited by examiner

ORTHOPEDIC KIT

The present invention relates to an improved kit for orthopedics, preferably for osteosynthesis.

As it is known, in the case of bone fractures, but also in corrective osteotomies and arthrodesis, making a surgical treatment of osteosynthesis, in which by means of a mechanical system of internal fixation are stabilized (immobilized) two or more bones heads (fragments) in order to allow bone healing.

The mechanical system to be used, besides being biocompatible, must be stable over time and must be suitably robust. In particular, this system must be suitably sized for the type and extent of the bone union to be made; in fact, if the implant is too light, it risks bending and deforming, while if it is too heavy, the bone is reabsorbed.

Moreover, the mechanical implant must be fixed to the bone in a stable manner, however this implant must not be too rigid as, to obtain an appropriate healing, it is necessary that the bone is appropriately stressed. In particular, the implant must be sized and implanted so that the stress of the physiological load partly reaches the area of bone discontinuity and this in order to stimulate the activity of the osteoblasts and therefore the development and consolidation of the bone.

The internal fixation mechanical implant generally comprises a plate which is fixed by screws to the respective bone ends to be immobilized. In particular, the plate consists of a plate that is fixed by screws to the bone fragments to be joined in order to stabilize them and stimulate them, thus allowing bone healing.

Among the known internal fixation implants to stabilize corner there is the so-called internal fixator "Fixin", which comprises three components: the plate member, the compass and the screw. More in detail, the compass has a threaded external side wall, to allow screwing within the threaded through holes of the plate, and a conical internal hole which cooperates with the corresponding conical head of the screw; moreover, the compass has a grooved collar which engages with the end of a corresponding instrument configured to screw/unscrew the compass into the hole of the plate.

In the internal fixer "Fixin" the plate is particularly weakened from the need to obtain inside it a threaded hole of increased diameter to allow the insertion of the compass. In particular, this makes the plate less resistant to both static stresses (for example, when it bends as the patient rises) and to dynamic stresses (for example, it breaks with fatigue, after about a month, when the patient walks).

Furthermore, in general, the removal of the present internal fixation mechanical systems is rather problematic.

Indeed, once any plate of a known system is implanted, it may happen that there is a need to remove it, for example, because the same plate is infected, bent or broken, or because some screws are broken or unscrew, or because it might cause the occurrence of tumoral forms, or because the bone is reabsorbed, etc. Currently, for the removal of the plate of the known internal fixation implants it is necessary to make a rather large cut on the skin and on the underlying tissues so as to be able to first access the individual screws, to remove them from the bone, so as to then proceed to the plate extraction through the cut made. In essence, this surgical operation for plate removal is particularly invasive, complicated and laborious, as well as having high morbidity and high risk of infections, as well as leaving extensive and apparent skin scars.

Another known internal fixation mechanical implant is described in PN2013U000037. In particular, this system provides for the use of a plate in which a plurality of through holes are made to be traversed by corresponding fixing screws which have, in sequence, a head, a flared portion (collar) and a self-tapping stem. More in detail, unlike the "Fixin" system, the system described in PN2013U000037 does not provide for the use of compasses since the holes in the plate themselves define a conical/flared housing for the corresponding conical/flared portion of the fixing screws. In essence, the stabilization of the implant is obtained by direct conical coupling between the plate and the screws.

Furthermore, the head of the fixing screws has the top a cavity delimited by a threaded inner wall which thus defines a threaded coupling for locking a first instrument, which acts as a screwdriver. In particular, by screwing the end of the screwdriver on the threaded coupling of the head, the screwdriver is made integral in rotation with the screw so that—following the further rotation of the screwdriver—the threaded portion of the screw is inserted into a corresponding bone fragment.

Appropriately, the screwing—caused by the action exerted on the screwdriver—of the screw within the bone limb continues until the flared portion of the screw itself engages within the corresponding flared seat of the through hole of the plate.

Furthermore, the head of the screw—which is substantially cylindrical or mushroom-shaped—has on its external wall, a thread for the engagement/fixing of a second and different instrument, which acts as an extractor. In particular, by screwing the end of the extractor onto the external wall of the screw head, the extractor is made integral with the screw so that—following the further rotation of the extractor—the threaded portion of the screw disengages from the corresponding flap bone.

In essence, the solution described in PN2013U000037 concerns a kit which, in addition to the internal fixation mechanical implant, also includes a first tool for screwing the screw into the bone fragment and a second instrument (which is completely distinct and independent of said first instrument) to unscrew the screw so to extract it from the fragment bone.

These known kits—which includes the plate, the screws, the screwdriver and the extractor—is particularly satisfactory, however its current mode of realization it is rather complicated and, moreover, the operations carried out to achieve the conical coupling between the holes of the plate and the collar of the screws do not allow to obtain high precision levels. In particular, the conical through holes made inside the plate do not reach the particularly narrow tolerances required by the context of application, tolerances which are generally of the order of one hundredth of a millimetre.

US2002/0120271 describes a device for stabilizing the vertebrae in the human spine. In particular, this device comprises a series of screws which engage in corresponding holes formed in a plate so as to keep the latter in contact with the vertebrae. More in detail, the screws have a threaded stem and a head which is entirely conical/flared and which is configured to substantially pass through the corresponding hole in the plate. In this solution, the screws are extremely difficult and complicated to remove.

US2013/0072984 describes a solution for bone fixation in which a screw to be inserted directly, without any plaque, into the desired bone area. In particular, this screw is externally threaded and has a hollow longitudinal passage inside it; furthermore, the screw head is externally threaded to allow its engagement by an insertion tool to be used to guide said screw into the desired bone area.

US2015/0216573 describes a cervical plate formed by an elongated asymmetrical body having one or more through openings which cross the plate from one face to the other; moreover, bone fixing screws are provided comprising a threaded stem and a head configured to be entirely housed within a corresponding through opening formed in the plate.

Purpose of the invention is to provide an improved kit for orthopedics, preferably for osteosynthesis, which overcomes the drawbacks of the traditional solutions and is an improvement and/or an alternative compared to said solutions.

Another object of the invention is to provide a kit in which the components can be made and machined with high precision, thus allowing a coupling between said components which is as stable as possible and free from play.

Another object of the invention is to provide a kit that is simple, quick and intuitive to use.

Another object of the invention is to provide a kit with an alternative characterization, both in constructive and functional terms, with respect to the traditional ones.

Another object of the invention is to provide a kit that can be obtained simply, quickly and at low cost.

Another object of the invention is to provide a kit that can be used on several pathologies and validated in the field of orthopedics.

Another object of the invention is to provide a high quality, robust, reliable, non-invasive and safe kit both for the operator and the patient.

Another object of the invention is to provide a kit that allows an easy and rapid removal of the mechanical fixing system.

All these aims, both individually and in any combination thereof, and others which will emerge from the following description, are achieved, according to the invention, with an improved kit for orthopedics, preferably for osteosynthesis, having the characteristics indicated in the claim 1.

In particular, the present invention relates to an improved kit (1) for orthopedics, preferably for osteosynthesis, comprising an internal mechanical fixing system (2) which comprises a plate (4) to be mounted straddling two bone fragments to be joined (7', 7") and at least two, preferably at least four, fixing screws (5) to fix the plate to said two bone fragments (7', 7"), said implant being characterized in that:

said plate (4) consists of a plate made of biocompatible metal material and has a thickness of about 0.5-4 mm, said plate (4) being provided with at least two, preferably at least four, conical through holes (8) whose inner walls (9) are obtained with at least one surface finishing mechanical operation, each of said at least two fixing screws (5) has a head (11) and a self-tapping stem (13) between which a conical collar (10) configured to define a conical coupling within a corresponding conical through hole (8) of the plate (4) is interposed, the head (11) presenting on its upper surface a recessed and shaped mark (15) for the coupling by the, at least partial, shape coupling, of the tip (32) of a screwing tool (31) and said head (11) also having on its external side wall (14) a thread (16) for the engagement of a gripping tool (35), and also characterized in that each of said at least two fixing screws (5) are configured so that, when its conical collar (10) is inserted into a corresponding conical through hole (8) of the plate (4), said head (11) protrudes externally with respect to said plate (4).

Advantageously, said kit also comprises a screwing tool (31) which is provided with:

a handle (36) to be gripped by the operator, e a stem (37) which is associated with said handle (36) and whose free tip (32) has a full shaped portion so as to be engaged, by the, at least partial, shape coupling, in the shape of the recessed mark (15) on the upper surface of the head (11) of the fixing screw (5) and so that, once engaged, the rotation of said tip (32) drags said screw (5) into rotation.

Advantageously, said kit also comprises a gripping tool (35) which is provided with a stem (38) which has a tubular end portion (40) which is internally hollow and is internally provided with a female thread (41) adapted to be screwed to the thread (16) provided on the external side wall (14) of the head (11) of the fixing screw (5).

Advantageously, said kit also comprises an adapter (42) for transforming the screwing tool (31) into a gripping tool (35), said adapter (42) comprising a tubular stem (38), internally hollow, inside which it is destined to be inserted the stem (37) of the screwing tool (31), said tubular stem (38) having a tubular end portion (40) which is internally hollow and is internally provided with a female thread (41) configured to be screwed to the thread (16) provided on the external side wall (14) of the head (11) of the fixing screw (5).

Advantageously, said kit also comprises a tensioning device (60) which comprises two members (61, 62), to be associated with two distinct bone fragments (7', 7"), and connected to each other so as to allow their mutual approach/removal, at least one of said two members (61, 62) is configured to be associated with said plate (4) by means of said gripping tool (35) which passes through and/or is associated with said member (61, 62) and which is screwed with its tubular end portion (40) onto the thread (16) of the head (11) of a screw (5) which, passing through a conical through hole (8) provided in said plate, fixes it to a corresponding fragment bone (7', 7").

Advantageously, said kit also comprises a tip centering device (50) which is configured to guide a drilling tip (51) so as to create in the bone (7', 7") a longitudinal cavity (52), inside which is intended to be inserted and housed the fixing screw (5), which is aligned with the axis that passes through the conical through hole (8) of the plate (4), said tip centering device (50) comprising a tubular element (53) with an internal channel (54) which is adapted to be crossed and to guide said drilling tip (51), said tubular element (53) presenting:

an end portion (55) which is conical and is shaped to engage within a corresponding conical through hole (8) of the plate (4) so that said internal channel (54) is aligned with the axis that passes through said conical through hole (8), at the other end portion, an inlet portion of said internal channel (54) which has a greater cross-section than the remaining, inner part, of said channel (54).

In particular, the present invention relates to a screwing tool (31) which is provided with:

a handle (36) to be gripped by the operator, and a stem (37) which is associated with said handle (36) and whose free tip (32) has a full shaped portion so as to be engaged, by the, at least partial, shape coupling, with the shape of the recessed mark (15) on the surface upper part of the head (11) of the fixing screw (5) and so that, once engaged, the rotation of said tip (32) drags said screw (5) into rotation.

In particular, the present invention relates to a gripping tool (35) which is provided with a stem (38) which has a tubular end portion (40) which is internally hollow and is internally provided with a female thread (41) suitable for being screwed to the thread (16) provided on the external side wall (14) of the head (11) of the fixing screw (5).

In particular, the present invention relates to an adapter (42) for transforming the screwing tool (31) into a gripping tool (35), said adapter (42) including a tubular stem (38), internally hollow, inside which the stem (37) of the screwing tool (31) is intended to be inserted, said tubular stem (38) having a tubular end portion (40) which is internally hollow and is internally provided with a female thread (41) suitable for being screwed to the thread (16) provided on the external side wall (14) of the head (11) of the fixing screw (5).

Moreover, the present invention relates to a tensioning device (60) which comprises two members (61, 62), to be associated with two distinct bone fragments (7', 7"), and connected with each other so as to allow their mutual approach/removal, at least one of said two members (61, 62) is configured to be associated with said plate (4) by means of said gripping tool (35) which passes through and/or is associated with said member (61, 62) engaging by screwing its tubular end portion (40) onto the thread (16) of the head (11) of a screw (5) which, passing through a conical through hole (8) provided in said plate, fix the latter to a corresponding bone fragment (7', 7").

In particular, the present invention relates to a tip centering device (50) which is configured to guide a drilling tip (51) so as to create in the bone (7', 7") a longitudinal cavity (52), inside of which the fixing screw (5) is intended to be inserted, tip centering device (50) which is configured to guide a drilling tip (51) so as to create a longitudinal cavity (52) in the bone (7', 7"), inside which the fixing screw (5), which is aligned with the axis that passes through the conical through hole (8) of the plate (4) is intended to be inserted and housed, said tip centering device (50) comprising a tubular element (53) with an internal channel (54) which is suitable to be crossed and for guiding said drilling tip (51), said tubular element (53) presenting:

an end portion (55) which is conical and is shaped to engage within a corresponding conical through hole (8) of the plate (4) so that said internal channel (54) is aligned with the axis that passes through said conical through hole (8), at the other end portion, an inlet portion of said internal channel (54) which has a greater cross-section than the remaining, inner part, of said channel (54).

Figure 2:
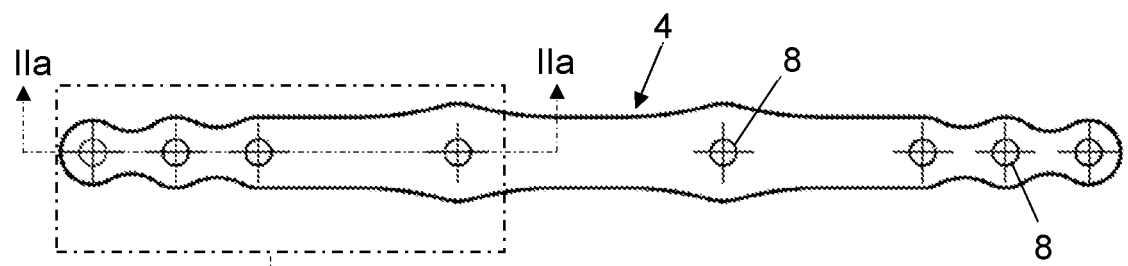
Figure 2A:
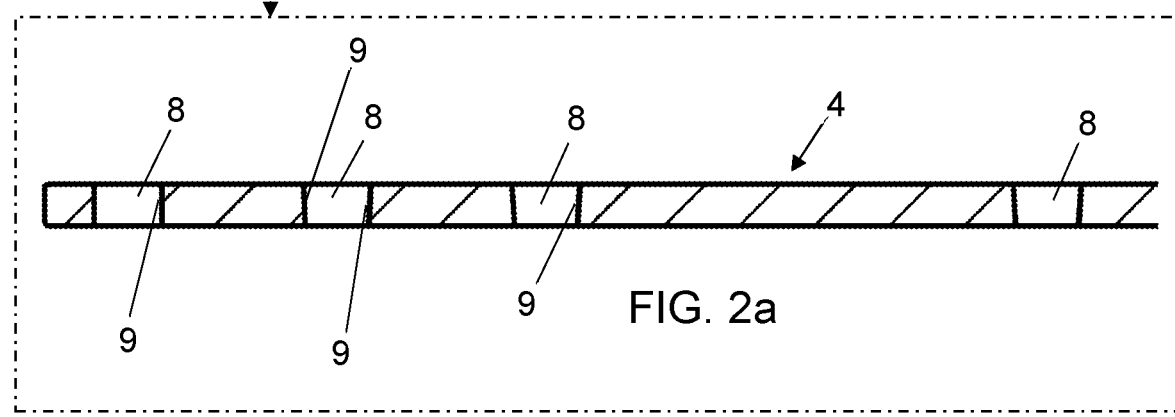
Figure 3:
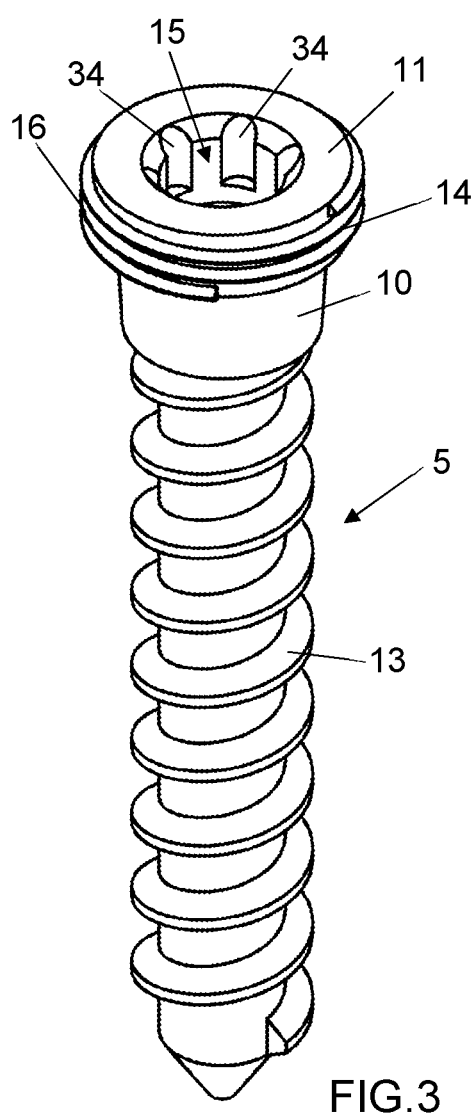
Figure 4:
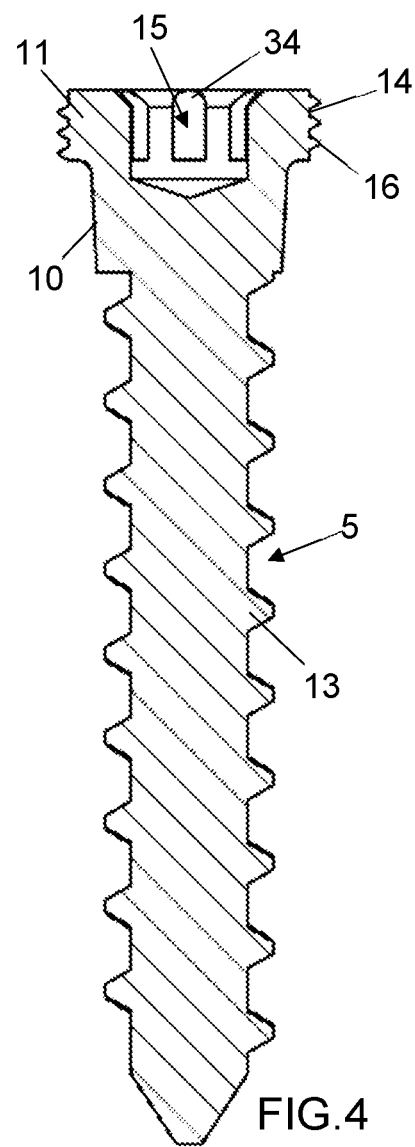
Figure 5:
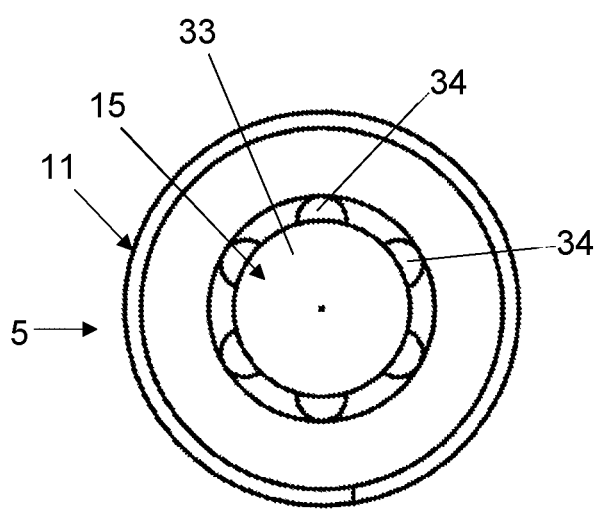
Figure 6:
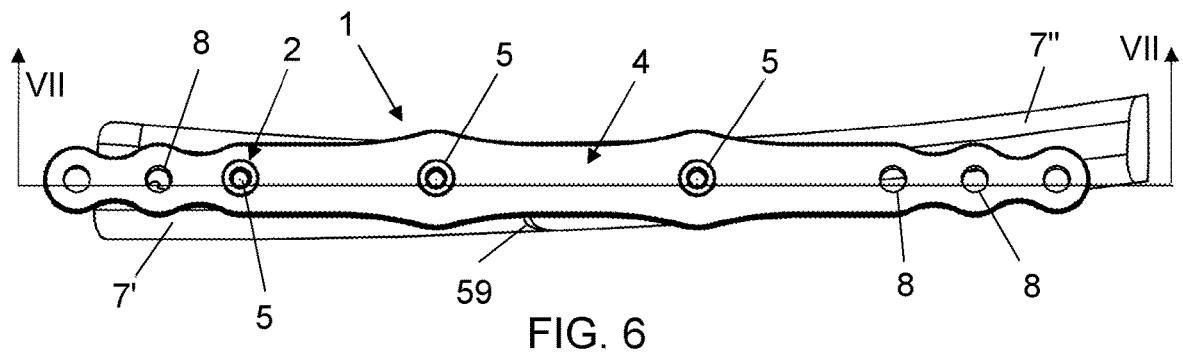
Figure 7:
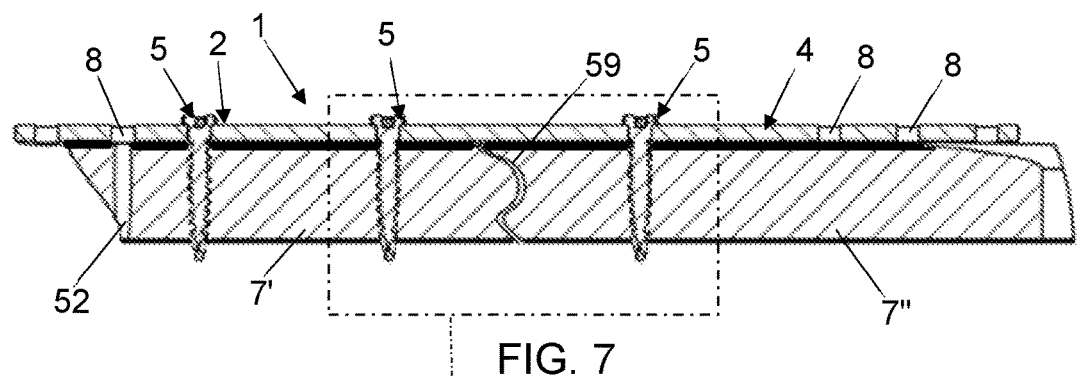
Figure 7A:
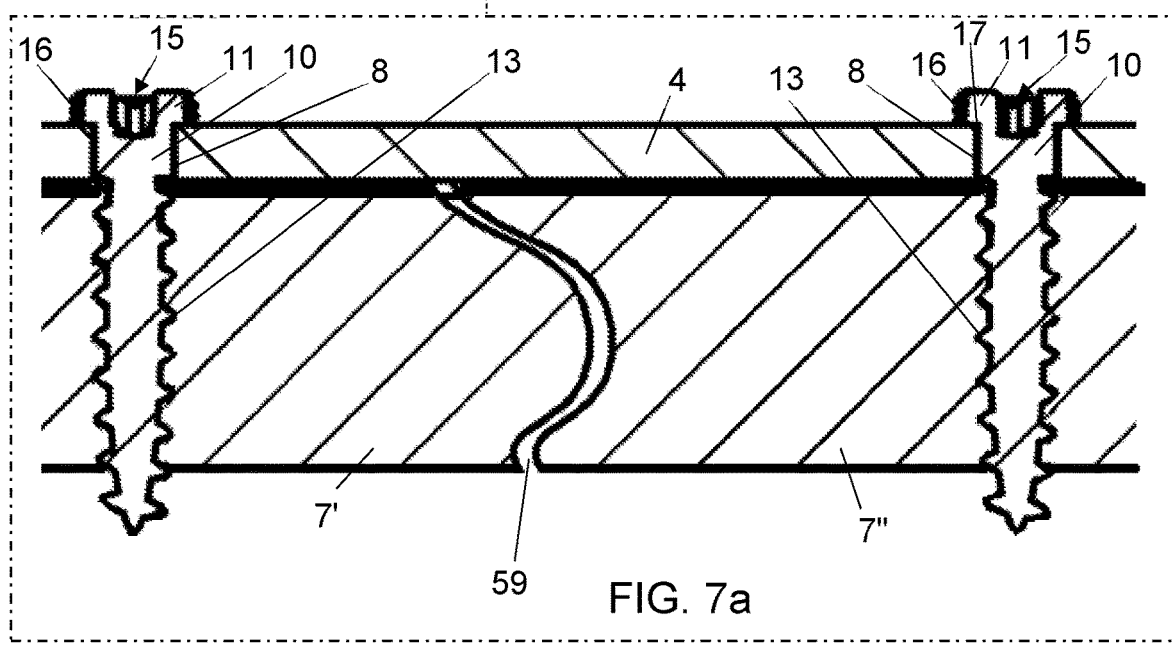
Figure 8:
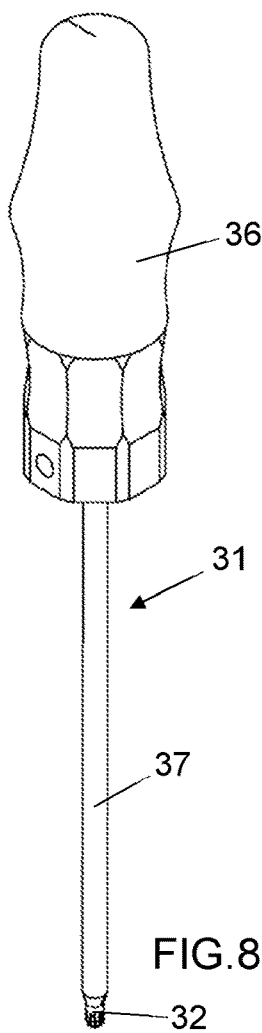
Figure 9:
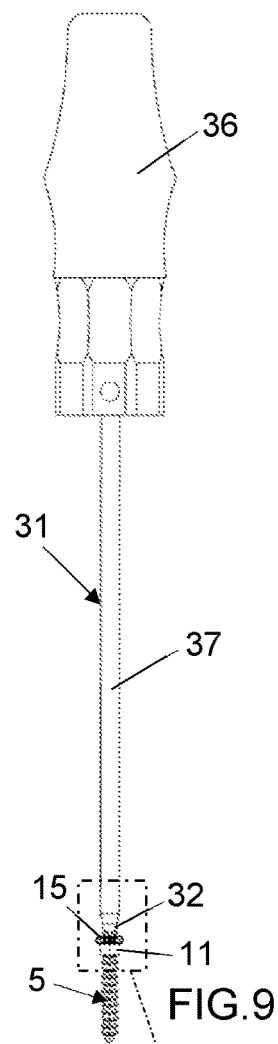
Figure 11:
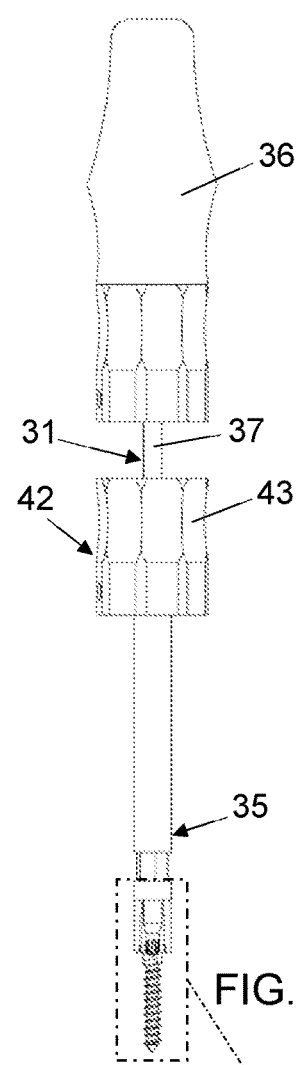
Figure 10:
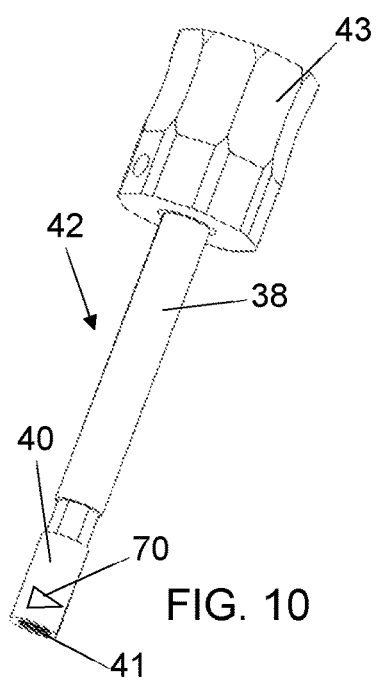
Figure 9A:
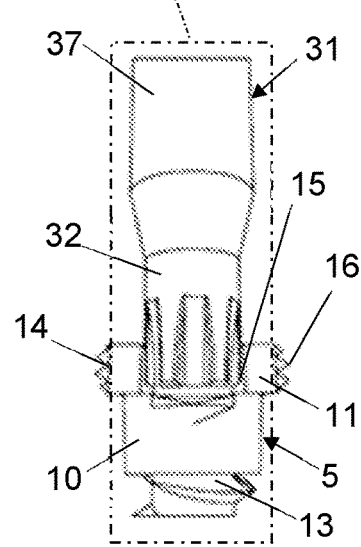
Figure 11A:
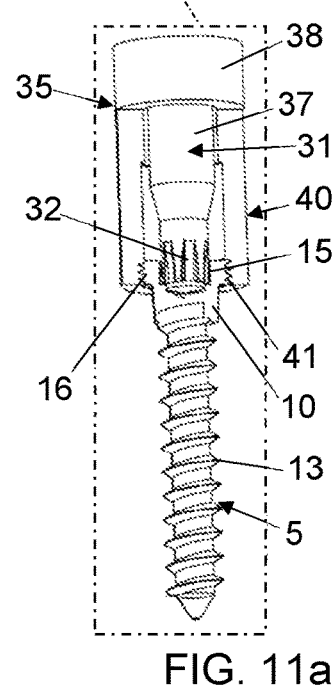
Figure 12A:
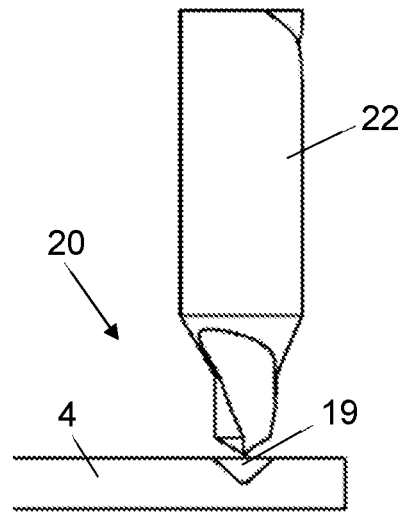
Figure 12B:
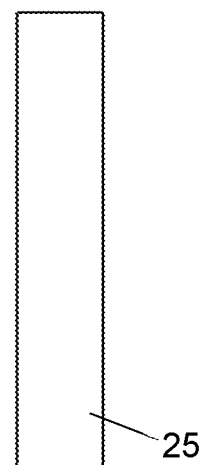
Figure 12C:
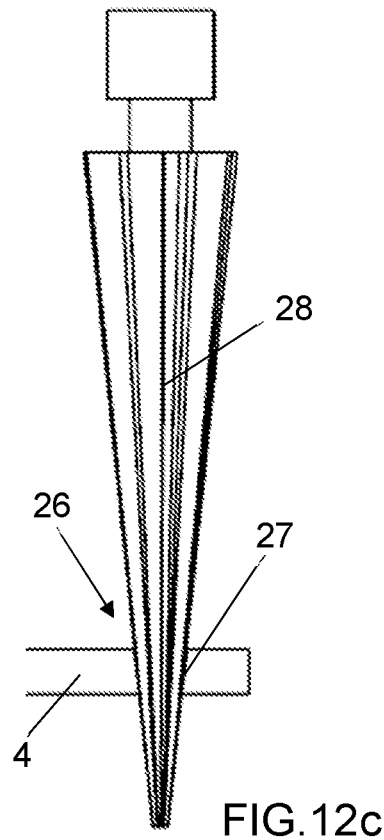
Figure 12D:
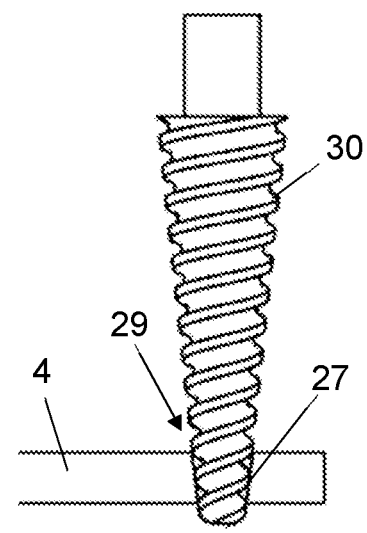
Figure 13:
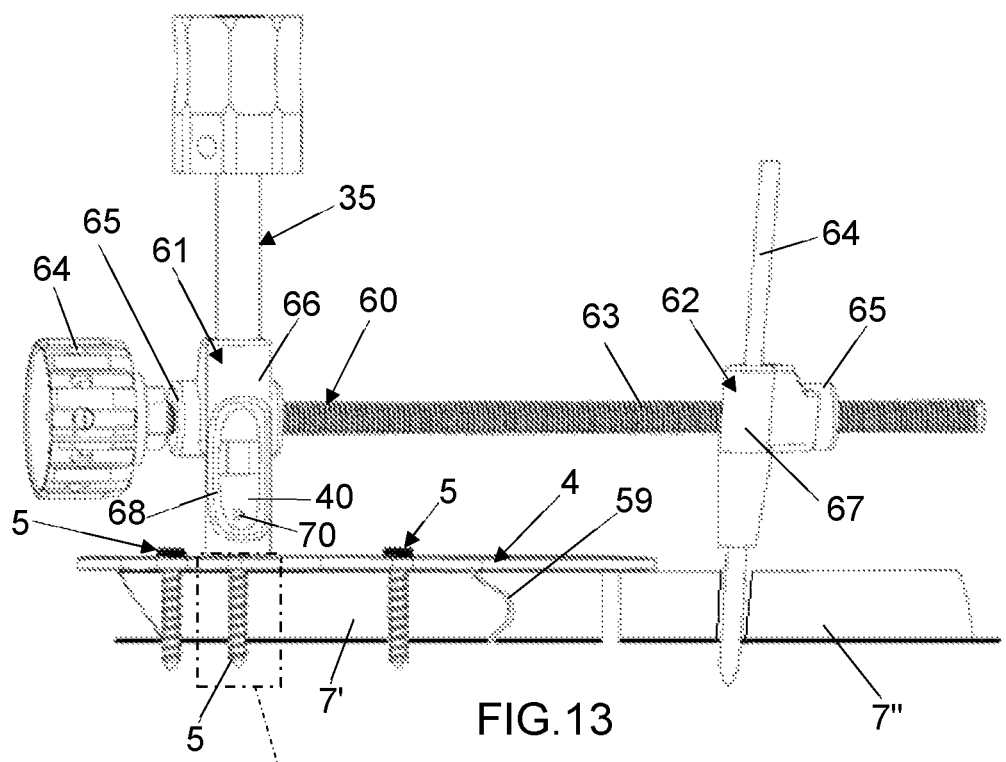
Figure 13A:
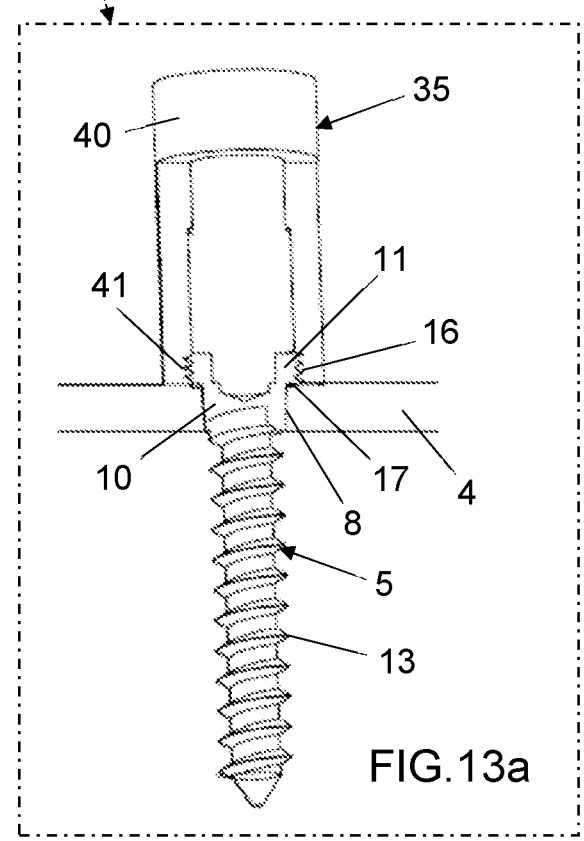
Figure 14:
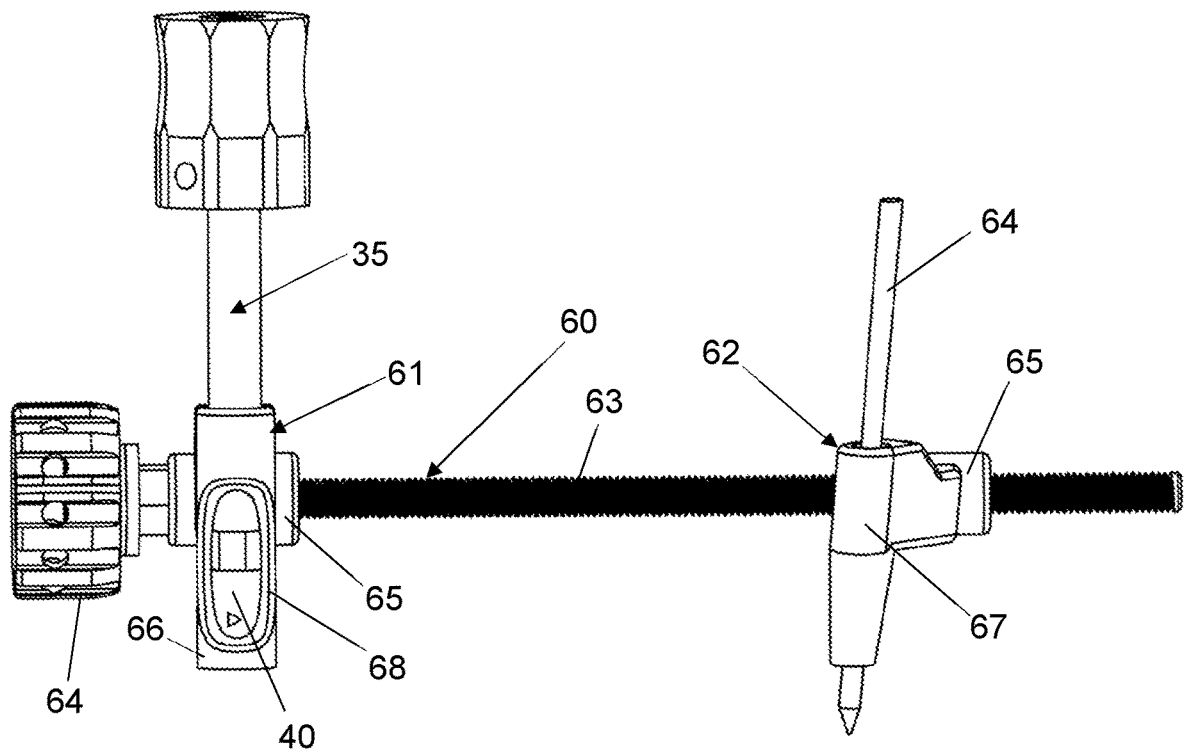
Figure 15:
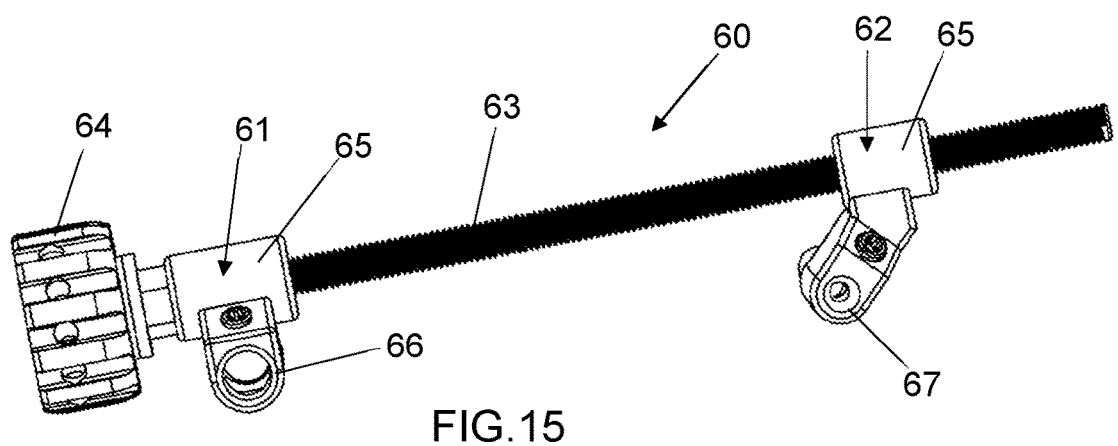
Figure 16:
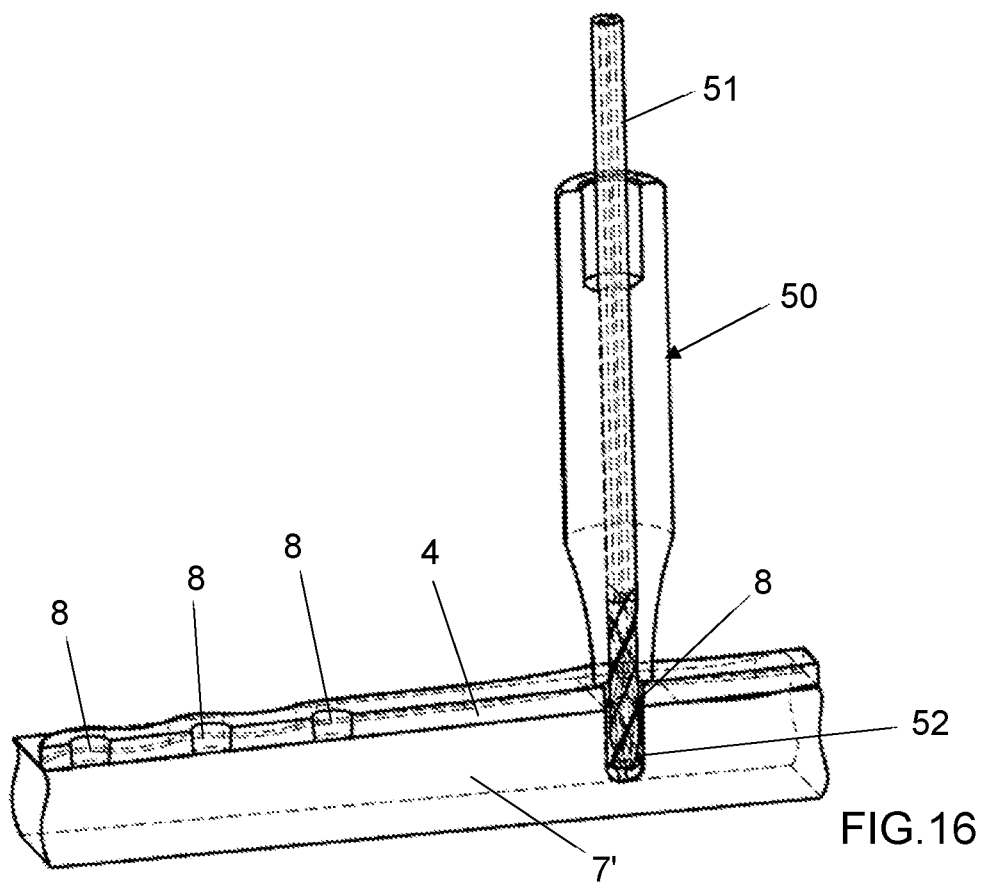
Figures 17, 18:
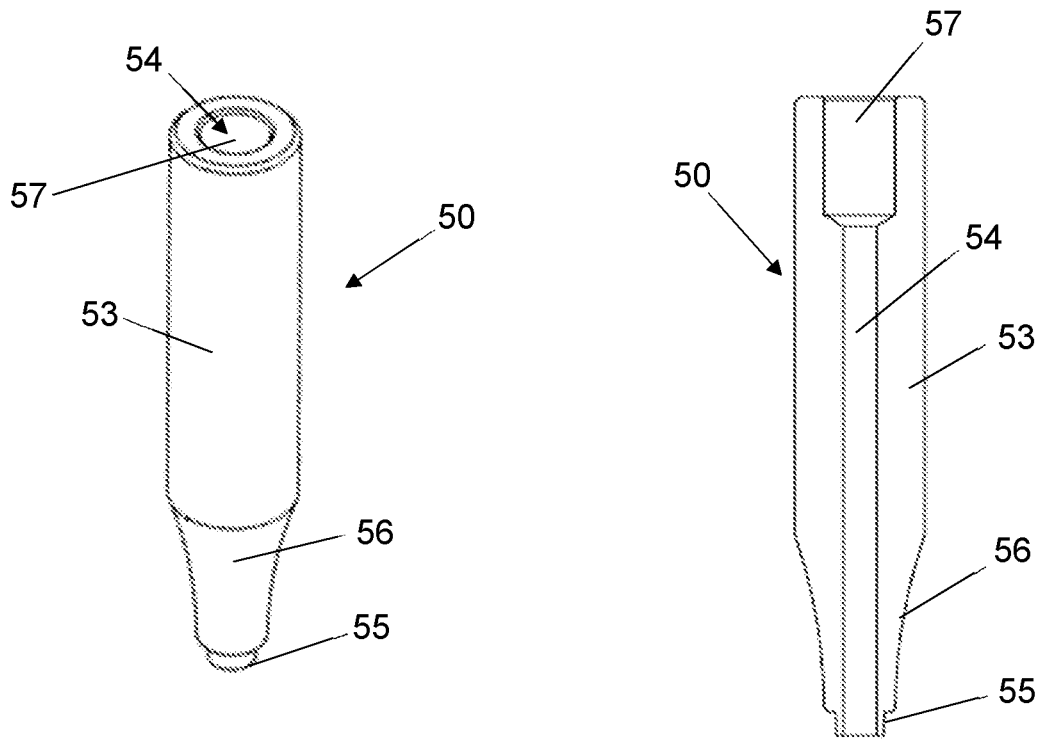

The present invention is further clarified hereinafter in a preferred embodiment thereof, given purely by way of a non-limiting example, with reference to the accompanying drawings, in which:

FIG. 1 shows in a perspective view from above the plate of the implant of the kit according to the invention, FIG. 2 shows, according to a plan view, the plate of FIG. 1, FIG. 2a shows an enlarged detail of the plate of FIG. 2 according to section IIa-IIa of FIG. 2, FIG. 3 shows in a perspective view from above a fixing screw of the implant according to the invention, FIG. 4 shows the fixing screw according to a section passing through its longitudinal development axis, FIG. 5 shows in a top view the head of the fixing screw, FIG. 6 shows according to a plan view the plate of FIG. 1 which is applied by means of the screws of FIG. 3 at a bone fracture, FIG. 7 shows section VII-VII of FIG. 6, FIG. 7a shows an enlarged detail of FIG. 7, FIG. 8 shows in perspective view a screwdriver of the kit according to the invention, FIG. 9 shows according to a side view the driver of FIG. 8 engaged with a fixing screw, FIG. 9a shows in partial section an enlarged detail of FIG. 9, FIG. 10 shows in perspective view an adapter for transforming the screwdriver of FIG. 8 in a gripping tool, FIG. 11 shows according to a side view the driver of FIG. 8 with the adapter of FIG. 9 engaged with a fixing screw, FIG. 11a shows in partial section an enlarged detail of FIG. 11, FIGS. 12a-d show in sequence, according to a side view, the tools to be used for making a flared hole on the plate of the kit according to the invention, FIG. 13 shows in perspective view a tightening device of the kit according to the invention with the relative means for fixing the members (tie-rods) of said device to the respective bone fragments to be joined, FIG. 13a shows in partial section an enlarged detail of FIG. 13, FIG. 14 shows in perspective view the tensioning device of FIG. 13 with the respective means for fixing the organs (tie-rods) of said device to the bone fragments to be joined, FIG. 15 shows in a different perspective view only the tensioning device of FIG. 14, FIG. 16 shows in perspective view a tip centring device which is crossed by a drilling tip and which is applied to a plate positioned on a bone fragment, FIG. 17 shows in perspective view a tip centring device a, and FIG. 18 shows it according to its longitudinal section.

As can be seen from the figures, the improved kit for orthopedics, preferably for osteosynthesis, generally indicated with the reference number "1" includes an internal mechanical fixing system 2 and at least one tool 31, 35 and 42 for its application, its handling/movimentation together with the bone and/or its removal.

The internal mechanical fixing system 2 includes a plate 4, to be positioned at the bone fragments 7' and 7" to be joined, and at least two fixing screws 5 (that is at least one screw for each bone fragment) to fix the plate to the corresponding bone fragments. Preferably, the internal mechanical fixing system 2 comprises at least two—preferably four—fixing screws 5 for each bone fragment. Preferably, all the fixing screws 5 of the internal mechanical fixing system 2 are equal to each other.

Conveniently, the plate 4 is made of biocompatible metal material, preferably in stainless steel, in particular in AISI 316LVM, or titanium alloy Ti6AI4V.

Conveniently, the fixing screws 5 are made of biocompatible metallic material, preferably of stainless steel, in particular of AISI 316LVM, or titanium alloy Ti6AI4V. The plate 4 comprises a plate of reduced thickness and, in particular, having a thickness of about 0.5-4 mm. Preferably, the plate 4 has a thickness of:

about 0.5-1.5 mm to be used with fixing screws 5 having an outer diameter of the stem 13 about 1.5 mm about 1.5-2 mm to be used with fixing screws 5 having an outer diameter of the stem 13 of about 2.5 mm, about 2-3 mm to be used with fixing screws 5 having an outer diameter of the stem 13 of about 3.5 mm, about 2.5-3.5 mm to be used with fixing screws 5 having an outer diameter of the stem 13 of about 4.5 mm.

Preferably, the plate 4 and the fixing screws 5 are made of biocompatible metal materials different from each other, for example the plate is made of steel while the screws are made of titanium alloy, or vice versa. Advantageously, in the case of a plate with a thickness of less than 0.5-1.5 mm, the plate and the screws are made of the same metallic material (for example in steel or in titanium alloy), while in the case of a plate with a thickness greater than 1.5 mm the plate and the fixing screws are made of different metallic materials.

Advantageously, the reduced thickness of the plate 4 allows its application at and in close proximity to the bone fragments to be joined 7' and 7" and, moreover, allows a suitable longitudinal flexibility of the same so as to stress the fragments to which it is applied; moreover, the reduced thickness of the plate 4 allows it to be positioned/implanted below the skin.

The plate 4 has at least two—preferably at least four—through holes 8 which pass through the plate from side to side (i.e. cross the thickness of the plate) and have a conical (i.e. substantially flared) shape. Conveniently, the conical through holes 8 define the seats for the insertion of the fixing screws 5, thus allowing the coupling of these with the plate 4.

Preferably, each conical through hole 8 of plate 4 it has an entirely conical shape, i.e. it is conical for its entire length along the thickness of the plate 4.

Preferably, each conical through hole 8 of the plate 4 has a diameter (defined at the minor section of the conical section) of about 1.5-4.5 mm. In particular, advantageously, the fact that the conical through holes 8 formed in the plate 4 have particularly small diameters (i.e., about 1.5-4.5 mm)—and in any case lower than those envisaged, with the same screw diameter being equal fixing, in traditional "Fixin" systems—makes the plate 4 more robust to both static and dynamic stresses.

Conveniently, the inner wall 9 which delimits the conical through hole 8 is not threaded.

Appropriately, considering as "internal surface" of the plate the one which—once the plate itself is implanted—is facing closer to the 7', 7" bone fragments and as the "external surface" the other surface (i.e. the opposite surface), it follows that—going from the outer surface toward the inner surface of the plate—the inner wall 9 which delimits each conical through hole 8 is slightly inclined/flared from the outside towards the intern.

Conveniently, the inner wall 9 which delimits each conical through hole 8 of the plate 4 is tilted/flared towards the interior of such an angle as to allow a suitable coupling with a corresponding conical portion 10 (i.e., the collar is interposed or between the head 11 and the stem 13) of the fixing screw 5, but at the same time it must not cause the joint of the latter since otherwise it would not be possible to remove the screw from the plate.

Advantageously, the inner wall 9 of each conical through hole 8 of the plate 4 is inclined of about 1°-2° with respect to the axis passing through the through hole, preferably it is inclined of about 1.5°.

Advantageously, the engagement of the conical portion 10 within the conical through hole 8 is of the self-centring type, thus automatically allowing the locking and the centring of the screw 5 within a corresponding hole 8 of the plate 4.

Conveniently, the development axis of the conical through hole 8 is coincident with or parallel to the axis perpendicular to the outer surface of the plate 4. However, suitably, the development axis of the conical through hole 8 can also be inclined with respect to the axis perpendicular to the external surface of the plate 4. In other words, the conical through hole 8 can have a development axis which is inclined from the outside surface to the internal surface of the plate 4.

Advantageously, the conical through hole 8 of the plate 4 it is not obtained exclusively by burr removal through the use of a reamer, but a surface finishing treatment is also provided by rolling so as to reach the required tolerance (i.e. of the order of one hundredth of a millimetre).

Preferably, each conical through hole 8 of the plate 4 is obtained in the following passages, in each of which a different tool is used.

In the first step (see FIG. 12*a*) a marking operation 20 is performed on the upper surface of the plate 4, and in particular a machining operation is carried out in order to obtain a starting hole 19 to then facilitate the insertion of the tool tip to be used in the next step. Advantageously, this marking operation 20 is carried out using a tool with a center point 22.

In the second step (see FIG. 12*b*), a cutting operation (drilling) 23 is carried out in order to obtain a cylindrical hole 24 which runs entirely through the thickness of the plate 4. Advantageously, this operation 23 is carried out by means of a tool with a helical tip 25, preferably with at least three cutting edges.

In the third step (cfr. FIG. 12*c*) performing a boring and/or reaming operation 26 intended to give a conical shape 27 to the previously obtained cylindrical hole 24. Advantageously, this operation is carried out by means of a reamer tool 28 with a conical tip. Conveniently, by means of this operation a pre-calibration of the conical hole to be obtained on the plate 4.

Conveniently, a fourth passage is finally provided (see FIG. 12*d*) in which a surface finish by rolling 29 is carried out on the conical-shaped hole 27 so as to achieve the required tolerance and, in particular, a tolerance of the order of the hundredth of millimetre. Advantageously, through the surface finishing by rolling 29 the inner wall of the conical-shaped hole 27 is plastically and gradually deformed so as to smooth it superficially, and thus obtain the conical through hole 8. Conveniently, by this operation the final calibration of the conical-shaped hole 27 is substantially carried out so as to bring it to the required precision or finish.

Conveniently, a conical tip 30 is used which is laterally shaped and, preferably, is of the step type.

Suitably, the finishing by rolling 29—which is a process that does not require any burrs removal—allows a low wear of the tool used for the corresponding processing and, moreover, allows a plurality of high precision conical through holes 8 to be made quickly in the plate.

Advantageously, the plate 4 has lateral swellings 12 at the area in which the conical through holes 8 are formed. Advantageously, the conical through holes 8 can be distributed symmetrically with respect to the central area of the plate 4 or they can also be distributed asymmetrically with respect to the transverse and/or longitudinal development of the plate itself.

Preferably, the plate 4 has a substantially elongated development (i.e. it is narrow and long). Appropriately, the plate 4 can comprise several portions—each provided with at least one conical through hole 8—which are aligned with each other or angled.

The fixing screws 5 comprise, in sequence, a head 11, a collar 10 and a conic or self-tapping stem 13 intended to be screwed into a corresponding longitudinal cavity 52 formed in the bone fragment 7' or 7". In particular, the conical collar 10 acts as a connection between the head 11 and the self-tapping stem 13.

Conveniently, the self-tapping stem 13 is configured to thread the cylindrical hole of the longitudinal cavity 52 formed in the bone fragment 7' or 7" during its screwing into said cavity. Preferably, the end of the self-tapping stem 13 can be pointy. Preferably, the body of the self-tapping stem 13 can be cylindrical or conical. Conveniently, the self-tapping stem 13 could also be self-drilling, i.e. capable of creating the longitudinal cavity 52 itself.

Conveniently, it is understood that the diameter of the cross-section of the longitudinal cavity 52 which is formed in the bone fragment 7' or 7" is slightly smaller than the external diameter of the self-tapping stem 13 of the screw 5 to be inserted in said cavity. For example, for a screw 5 with an external diameter of the self-tapping stem 13 of about 2.5 mm, the diameter of the cross-section of the longitudinal cavity 52 obtained on the bone fragment will be about 2 mm.

Advantageously, the self-tapping stem 13 has a groove at the tip to perform a tapping action on the longitudinal bone cavity 52 for preparation.

Conveniently, the head 11 has an external side wall 14 of a certain height (preferably of about 0.5-2 mm) and, preferably, is substantially cylindrical or mushroom-shaped.

The head 11 has on its surface greater than a recessed and shaped mark 15 (recess) for engagement—by the, at least partial, shape coupling—of the tip 32 of one or screwing/unscrewing tool 31 (hereinafter referred to as "threading tool" For simplicity).

Preferably, the tip 32 of the screwing tool 31 has a solid portion which is shaped correspondingly, i.e. substantially complementary, to the shape of the recessed mark 15. In essence, the shaped tip 32 of the screwing tool 31 defines a male element that is inserted within a female element which is defined by the shaped recessed mark 15 that is formed on the upper surface of the head 11 of the fixing screw 5.

Advantageously, the fact that the head 11 presents a recessed mark (recess) 15 and shaped for engagement by coupling, at least partial, of the shape of the tip 32 of the screwing/unscrewing tool 31 ensures the buoyancy perpendicularity between the screw head and the threading tool, thus allowing to reduce and avoid the risk of stripping said mark 15.

Advantageously, the recessed mark 15 can be shaped like a cross, square, hexagonal (Allen), cross-shaped with misalignment or star-shaped axes.

Preferably, the recessed mark 15 is of the type known under the trade name "Torx", hereinafter "Torx imprint", which is standardized in the ISO10664 standard with the name "hexalobular internal seat for screws" and substantially presents a star-shaped with six points. In particular, the Torx footprint is particularly advantageous as it allows:

to withstand a higher torque, a quick and rapid centering of the screwdriver tool tip the perpendicularity of the trim between the screw head and the screwing tool, and this is a determining factor considering that the stem of the fixing screw is self-tapping, guarantees, during the tightening phase, a stable and safe coupling with the screwing tool, eliminating in particular the risk that the tip of the latter comes out of the Torx mark.

In particular, the fact that the recessed and shaped mark 15 is not internally threaded (such as for example in the solution presented in PN2013U000037) avoids problems of stripping as a result of the engagement of the tip of the screwdriver within said coupling.

Advantageously, the recessed and shaped mark 15 of the head 11 has a hollow central portion 33, preferably substantially cylindrical, which is surrounded by lateral discharge grooves 34 which are not provided in the corresponding full shape defined by the tip 32 of the screwing tool 21. Appropriately, a part of the solid fibrous material that has settled inside the recessed and shaped mark 15, is pressed on the bottom of the latter by the tip 32 of the screwing tool 31 while the discharge grooves 34 define recesses in which—by means of the tip 32 of the screwing tool 31—the liquid or fluid fibrous material is pushed, which deposits inside the recessed and shaped mark 15, so as to cause it to escape from the same mark through said grooves 34. Substantially, in this way, the head 11 of the screw 5 is cleaned from the fibrous material or bone that has settled following the application of the screw itself in the bone; in particular, this cleaning is carried out during the first implantation phase of the screw on the bone but, most important, on the occasion of its eventual removal from the bone itself.

Advantageously, the discharge grooves 34 can be formed at the points of the star-shaped shape of the recessed mark 15 shaped like a torx.

Suitably, as mentioned, the head 11 of each screw 5 presents along/on its external side wall 14 a thread 16 for engagement/fastening of a gripping (extracting/manipulating) tool 35. In particular, by screwing the ends of or gripping tool 35 on the threaded external side wall 14 of the head 11 of the screw 5, it makes the tool integral with said screw 5; conveniently, in this way, by moving the gripping tool 35, the operator can pull, move and displace the bone fragment 7' or 7" in which the stem 13 of the screw 5 is inserted, whose head 11 has been made integral with said tool 35.

Conveniently, the thread 16 of the threaded external side wall 14 of the head 11 of the screw 5 is helical, and it develops in the opposite direction with respect to that of the rotation to be imparted to the screw itself in order to screw the self-tapping stem 13 into the bone fragment 7' or 7". Conveniently, the thread 16 of the external side wall 14 of the head 11 of the fixing screw 5 is a left helix.

Suitably, the gripping tool 35 is configured to be screwed to the thread 16 of the threaded external side wall 14 of the head 11 of the screw 5 until the tubular end portion 40 of said instrument enters into abutment with the outer surface of the plate 4—around the screw itself.

Advantageously, the engagement by screwing between the gripping tool 35 and the head 11 of the fixing screw 5 allows a more stable constraint between them, thus allowing to be able to exert a greater force on the instrument both for extraction and for manipulation.

Conveniently, moreover, the fact that the head 11 of the screw 5 on its external side wall 14 has a thread 16 which allows the suture thread to be anchored around the latter to draw near the tissues or to close the skin.

The collar 10 of the fixing screw 5 has a conical shape which is configured—both in terms of shape and size—to be inserted and coupled stably but removably within a corresponding conical through hole 8 formed in the plate 4.

In essence, the coupling between the collar 10 of the fixing screw 5 and the conical through hole 8 of the plate 4 is of the conical type. Suitably, the conical coupling between the collar 10 of the screw 5 and the conical through hole 8 ensures the stable locking of the internal mechanical fixing system 2 (which includes the plate 4 and the screws 5) of the fragments bone 7' and 7", thus guaranteeing the stable fixation of the latter.

In particular, the fixing screw 5 is configured so that, when the collar 10 of said screw is engaged/locked in the conical through hole 8 of the plate 4, the head 11 protrudes/leak externally at least in part—preferably entirely—with respect to the plate itself, and in particular protrudes from the outer surface of said plate (see FIGS. 7a and 13a). Preferably, the head 11 of each fixing screw 5 has a flange 17 for the connection with the collar 10 and, appropriately, said flange 17 is designed to protrude and be slightly spaced (for example of about 0.1 mm) with respect to the to the outer surface of the plate 4 when the conical collar 10 of the fixing screw 5 is inserted or within the conical through-hole 8 of the plate itself. Preferably, the flange 17 has a substantially flat development (horizontal or slightly inclined) and is destined to be slightly spaced from the more external surface, substantially flat, provided in the plate 4 around the conical through hole 8.

The fact that the head 11 of the fixing screw protrudes beyond the plate 4 is particularly advantageous in that it allows the engagement of the tubular end portion 40 of the gripping tool 35 (as described more extensively below) and, in particular, this is useful during the step of extraction of the screw which, in fact, can take place both by means of the gripping tool 35 and—as a last attempt—also by means of handles or pincers which engage/grip with the respective jaws the head 11 which protrudes from the plate 4.

Conveniently, in the kit 1 and, in particular, in the system 2, no compassing or other supporting elements are provided for the engagement of the screw 5 with the plate 4. In other words, advantageously, the fixing system 2 it consists only of plate 4 and fixing screws 5.

The screwing tool 31 (see. FIGS. 8 and 9) comprises an ergonomic handle 36, intended to be gripped by the operator, and a stem 37 that is fixed to the handle and that—as said—in correspondence of its free tip 32 presents a solid portion which, preferably, is shaped in a corresponding manner, i.e. substantially complementary with respect to the shape of the recessed mark 15 on the upper surface of the head 11 of the fixing screw 5 (see FIG. 9a). Appropriately, the screwing tool 31 can be a traditional screwdriver whose tip has—preferably—a solid portion which is shaped in a corresponding manner, that is substantially complementary with respect to the recessed mark 15 on the upper surface of the head 11 of the fixing screw 5.

Advantageously, the engagement/interlocking of the free tip 32 of the screwing tool 31 within the recessed mark 15 provided in the head 11 of the fixing screw 5 causes—once the screw has been taken and the aforementioned engagement/engagement is performed—the screw itself can reach the operating table, without falling, during the operations that precede its insertion into the conical through hole 8 of the plate 4 and its screwing into a corresponding longitudinal cavity 52 formed in the bone fragment 7' or 7".

Advantageously, the kit 1 according to the invention also comprises a tip centering device to 50 (see FIG. 16-18). In particular, the tip centering device to 50 is a device configured to drive a drilling tip 51 of a drill or of another punching tool (not shown) so as to create in the bone 7' or 7" a longitudinal cavity 52 (inside of which the fixing screw 5) is intended to be inserted and housed, which is aligned (in axis) with the conical through hole 8 of the plate 4. Suitably, to this end, the tip centering device to 50 is substantially a tubular element 53 with an internal channel 54 that is suitable to be crossed and to guide the drilling tip 51 of the drill or other puncher tool.

Moreover, the tubular element has an end portion 55 which is conical and is shaped to be complementary to and engage within a corresponding conical through hole 8 of the plate 4 in such a way that said internal channel 54 is aligned with the axis that passes through said conical through hole 8. Suitably, going from the tubular body of the element 53 towards the conical end portion 55, a tapered connecting portion 56 can be provided.

Advantageously, at the other end portion (i.e. the opposite portion with respect to the conical end portion 55) of the tubular element 53, the internal longitudinal channel 54 has an inlet portion 57 which has a larger cross section (i.e. wider) than the remaining part (more internal) of channel 54. Preferably, the section of the inlet 57 is shaped like a funnel. Suitably, the fact that the tip centering device 50 presents such a widened inlet portion 57 allows to spray more (and thus cool) the tip 51 of the drill, piercer or tool, which overheats as a result of and during the cutting operation used to make the longitudinal cavity 52 in the bone 7' or 7".

So, to fix the plate 4 to a fragment bone 7' or 7" by means of one or more fixing screws 5 the following operations are performed:

positioning the plate 4 on the bone fragment and temporarily immobilizing it manually or by means of a suitable tool (for example a pair of pliers or a nail), fitting inside the conical through holes 8 of the plate 4 a tip centering device 50; in particular, the conical end portion 55 of the tip centering device is inserted at 50 within a corresponding conical through hole 8 of the plate 4, inserting the drilling tip 51 connected to a drill, or to another punching tool, within the internal channel 54 of the tip centering device so as to obtain on the bone a longitudinal cavity 52 which is aligned with the axis of a hole 8 of plate 4; suitably, the longitudinal cavity 52 has a slightly smaller diameter (or cross section) than that of the stem 13 of the fixing screw 5 to be inserted, the tip centering device 50 is then removed from the plate (as well as the drilling tip 51) and, by means of the screwing tool 31, the fixing screw 5 is inserted into the conical through hole 8 of the plate 4 and is made to rotate so that its self-tapping stem 13 engages within the longitudinal cavity 52 thus created in the bone fragment 7' or 7".

Preferably, more in detail, to screw the self-tapping stem 13 of each fixing screw 5 into the bone fragments 7' and 7", the screwing tool 31—once its tip 32 has engaged in the recessed and shaped mark 15 obtained on the head 11 of the screw 5—is rotated in a clockwise direction. Conveniently, the rotation action performed by means of the screwing tool 31 continues until the conical collar 10 of the fixing screw 5 fits into abutment and is coupled within the corresponding conical through hole 8 formed in the plate 4.

The gripping tool 35 comprises an ergonomic handle, intended to be gripped by the operator, with its own stem 38 which, at its free tip, has a tubular end portion 40 which is internally hollow and internally is provided with a nut screw 41 designed to be screwed to the thread 16 formed on the external side wall 14 of the head 11 of the fixing screw 5. Preferably, the female thread 41 of the tubular portion 40 of the gripping tool 35 is left-handed and, therefore, in order to screw the latter to the head 11 of the fixing screw 5 it is necessary to rotate the gripping tool in an anti-clockwise direction.

Conveniently, the rotation action carried out by the gripping tool 35 continues until the tubular end portion 40 of the latter abuts with the plate 4, thus making the gripping tool integral in rotation with the fixing screw 5. Therefore, the further rotation effected by the gripping tool 35 first causes the decoupling/disengagement (due to the axial component of the helical movement) of the conical collar 10 of the fixing screw 5 from the corresponding conical through hole 8 of the plate 4 and then causes the fixing screw 5 to be unscrewed from the corresponding bone fragment 7' or 7"; suitably, the screw 5 is extracted from the bone fragment 7' and/or 7" by unscrewing it with the same pitch used for its insertion and this avoids damaging the threads of the nut screw of the longitudinal cavity 52 (which defines the bony hole) and to cause the latter to be enlarged.

Advantageously, in an embodiment not represented, the screwing tool 31 can be a completely different and separate instrument from the gripping tool 35, that is, two instruments are provided each with its handle.

Advantageously, in the embodiment represented here (see FIGS. 10 and 11), the gripping tool 35 comprises an adapter 42 for transforming the screwing tool 31 into said gripping tool 35. In particular, this adapter 42 comprises a tubular stem 38, internally hollow, inside which the stem 37 of the screwing tool 31 is inserted to allow the pointing and the quick/easy engagement of the gripping tool 35 on the head 11 of the screw 5. Advantageously, in this way, as will become clearer below, the screwing tool 31 substantially acts as a pointer/stabilizer and as an internal guide element for the adapter 42 which acts as a gripping tool 35.

Suitably, the tubular stem 38 adapter 42 terminates with the tubular end portion 40 which is internally hollow and is provided internally with the female thread 41, as described above. Conveniently, the tubular stem 38 can be associated with a connecting portion 43 which extends the handle 36 of the screwing tool 31. Conveniently, it is understood that the adapter 42 is configured—and in particular its tubular stem 38 is dimensioned—so that, once it has been inserted into the screwing tool 31, the shaped solid tip 32 of the latter fits into the contoured and recessed mark 15 of the head 11 of the screw 5, thus facilitating positioning and the coupling on the latter also of the tubular end portion 40 of the tubular stem 38 of the adapter 42. Advantageously, using the adapter 42 and thus inserting the full shaped tip 32 of the screwing tool 31 into first the tubular stem 38 of said adapter and then entering the contoured and recessed mark 15 of the head 11 of the screw 5 facilitates the screwing of the female thread 41 of the tubular stem 38 of the adapter 42 to the thread 16 of the external side wall 14 of the head 11 of the screw 5.

Generally, to carry out the removal of the internal mechanical fixing system 2, only the screwing tool 31 is used.

In particular, to carry out the removal of the internal mechanical fixing system 2, the operator generally palpates the skin—in correspondence with the body area where the internal mechanical fixing system 2 was positioned—to identify the protrusion of the head of the fixing screws 5. Then, once this protrusion has been identified, the operator makes a skin and subcutaneous incision over the recessed mark 15 of the head 11 of the screw 5 and this in order to allow the insertion of the tip 32 of the screwing tool 31 and the engagement of said tip in the mark 15.

Conveniently, it is intended that in order to carry out the removal of a internal mechanical fixing system 2 which is positioned well below the skin (for example, in the case of the femur, the humerus and the pelvis the internal mechanical fixing system 2 is at a depth of approximately 4-6 cm below the skin), the operator first carries out skin incision in a body area suitable for the access and then moves the various tissues (muscles, tendons, vessels and nerves) in order to create a corresponding passage; then, palpates the head 11 of the screws 5 and insert the tip 32 of the screwing tool 31 through the skin incision and the passage thus defined until it engages it within the recessed and shaped mark 15 of said head 11.

Therefore, in both cases, once the tip 32 of the screwing tool 31 has engaged in the recessed and shaped mark 15 formed on the head 11 of the screw 5, said instrument is rotated counter clockwise (or in any case in the opposite direction compared to that used to insert the screw into the bone fragment) in order to extract/decouple the screw either from the longitudinal cavity 52 obtained in the bone fragment 7' or 7" and from the conical through hole 8 made in the plate 4.

The exit from the skin of the head 11 of the screw 5, and the remaining part of the screw 5 (that is, of the collar 10 and of the self-tapping stem 13), is favored by the thread 16 of the external side wall 14 which allows the screw itself to pass through the tissues without lifting them. Suitably, in other words, the thread 16 of the external side wall 14 of the head 11 of the screw 5 allows to extract the screw itself by making a particularly reduced and minimally invasive incision on the skin.

In some cases—for example when the screw 5 is deeply inserted in the bone fragment 7' and/or 7" and/or when the conical coupling between the collar 10 of the screw and the conical through hole 8 of the plate defines a joint difficult to remove and/or when the recessed mark 15 is stripped,—to carry out the mechanical removal of the internal mechanical fixing system 2 is used, in addition or as an alternative to the screwing tool 31, the gripping tool 35, which obviously requires of make a cutaneous cut slightly larger than the one necessary in the case of using only the screwing tool 31. Therefore, also in this case, once the protruding raised portion of the head 11 of the fixing screws 5 has been identified, the operator carries out a skin incision, or enlarges the previously performed one, so as to allow the insertion of the gripping tool 35 which is screwed with its tubular end portion 40 on the external side wall 14 of the head 11 of the fixing screw 5 so that the female thread 41 of the first engages with the thread 16 of the second. Therefore, once the gripping tool 35 is made integral with the fixing screw 5, this is further rotated so as to unscrew the stem 13 of the screw 5 from the bone fragment 7' or 7" in which it was inserted.

Once the stem 13 of the screw 5 has been unscrewed from the bone fragment 7' or 7", the screw itself—which still has its head 11 screwed to the gripping tool—is removed and extracted through the effected skin incision.

Conveniently, it is understood that these operations are carried out for each screw 5 used to fix the plate 4 to the bone fragments 7' and/or 7".

Once all the fixing screws 5 have been removed, the plate can be easily removed by pulling it out and passing it through one of the incisions made to remove the screws themselves, possibly after having slightly widened at least one of said incisions.

Advantageously, as stated, in order to remove the internal mechanical fixing system 2, the adapter 42 which transforms the screwing tool 31 into a gripping tool 35 can be used. With this scope, therefore, first the stem 37 of the screwing tool 31 is inserted in the tubular stem 38 of the adapter 42 and, with these two instruments thus joined, the screw 5 to be removed is approached.

Conveniently, moving away the tubular end portion 40 of the adapter 42 (for example holding it raised with a finger), from the tip 32 of the screwing tool 31, makes so that said tip 32 engages within the recessed and shaped mark 15 of the head 11 of the screw 5 to be removed.

Thus, when the stem 37 of the screwing tool 31 is aligned with the screw 5, i.e. when the tip 32 of the first is well inserted into the shaped recessed marks 15 of the second, the tubular end portion 40 of the adapter 42 is approached to the head 11 of the screw 5 and the female thread 41 of said portion 40 is screwed to the threads 16 provided on the external side wall 14 of the head 11 of the screw 5. In particular, for this scope, the adapter 42 is rotated counter-clockwise until its tubular end portion 40 comes into contact with the upper surface of the plate 4. Therefore, once the adapter 42 is made integral with the fixing screw 5, said adapter is further rotated—in a manner substantially corresponding to those described above for the gripping tool 35—so as to unscrew the stem 13 of the screw from the fragment bone 7' or 7" in which it was inserted.

Advantageously—in contrast to the traditional system of the type Fixin, wherein the through holes on the plate are internally threaded to allow the screwing of corresponding compasses—in the solution according to the present invention, the through holes 8 of the plate 4 are conical and are substantially smooth/polished internally (i.e. not threaded). This is particularly advantageous since the smooth conical hole 8 is easier to clean, while the threaded hole of the Fixin implant must be cleaned and disinfected with extreme care since otherwise it could cause infections; in particular, the Fixin implant plate with the internally threaded holes must be thoroughly cleaned and sterilized in order to eliminate the biological material that is inserted between the threads and which is the trigger for biofilms that infect the system itself.

It can happen that the operator who has chosen a plaque, after it has been positioned in correspondence with the area to be treated (and hence after provoking the contact of the plate itself with the biological material), sees that the choice plate is not suitable for that specific surgical treatment and, therefore, may decide to remove it immediately. However, in this situation, the plate—which has already come into contact with the biological material of the patient—or is definitively discarded, thus causing an undesirable waste, or—to be reused—must be properly cleaned by removing and washing all the compasses, then washing the plate itself and finally reassembling the compasses on the plate.

Therefore, it can be understood how—in this context— the present solution is more advantageous since, as mentioned, the fact that the plate 4 has non-threaded conical holes 8 makes its cleaning quicker, easier and simpler.

Advantageously, the kit 1 according to the invention also comprises a tensioning device 60 which comprises two members 61 and 62 connected together so as to allow their mutual approach/removal, thus generating a greater or inferior tension.

Conveniently, once the two members 61 and 62 are fixed to the respective bone fragments 7' and 7" to be joined, the actuation of the tensioning device 60 causes the two members 61 and 62 to move closer together, and thus the compression (also called "interfragmentary compression") at the contact area 59 (which consists for example of the fracture gap) between the bone fragments to which these organs are fixed.

In particular, as is known, the intra-fragmentary bone compression allows important biological and mechanical advantages for the osteosynthesis operation and, more precisely, favours the neovascularization of the bone fragments at their union zone. In fact, more in detail, from a mechanical point of view, the intra-fragmentary compression causes and increases the adherence of the bone heads and the stability of the system envisaged for the healing of the fracture, thus minimizing the play and the excursion of the fracture gap, reducing also considerably the static and dynamic stresses on the system; furthermore, from a biological point of view, the union of the bone fragments stimulates and promotes the cooperation between the blood vessels of the respective bone fragments. For these reasons, interfragmentary bone compression is highly recommended when an osteosynthesis operation has already failed.

Currently, to cause interfragmentary compression is already known to use a special plate that has one or more dedicated and eccentric holes in which engage the fixing screws. However, this known system makes it possible to obtain a distance between the bone fragments of about 1 mm or a maximum of 2 mm (in the case of two eccentric holes straddling the fracture gap to be joined). This is not always sufficient and, in particular, there are cases in which there is a need to create approach displacements between the bone fragments, in correspondence of the metaphysis area, for example greater than 2 mm (in particular of 2.5-3 mm).

Moreover, currently, in order to cause intra-fragmentary compression, a dedicated tensioning device is generally used which is exclusively designed to create the desired compression situation between the bone fragments and, once reached, this position is maintained by inserting traditional fixing screws. In particular, a known tensioning device requires the use of a plate which is positioned straddling the fracture gap (or bone fragments to be joined); therefore, a first extremal portion of the plate is fixed to a first fragment bone with one or more fixing screws, while on the other end portion of the plate—which acts on the second bone fragment to be joined—a bracket is attached and fixed which is connected by a rotating bolt to a guide slider for a nail that is inserted into the second bone fragment to be joined. Then, by rotating the bolt, the bracket hooked to the plate (and fixed to the second bone fragment by means of the nail) causes the movement of the first fragment towards the second fragment through the plate and then the bone compression between them.

This known tensioning device is not completely satisfactory since it is rather complicated and laborious to use. Moreover, this device is rather invasive and, in particular, requires that the plate is oversized in length so that it has dedicated areas for attaching the bracket of the tensioning device, areas which are currently distinct from those provided for insertion of the fixing screws.

Furthermore, when there are other tissues around the bone fragments, such as muscles or ligaments, there is a need to move the tensioning device so as to move it away from the plate. However, the various already known tensioning devices are not suitable to be easily moved towards or away from the outer surface of the plate.

In this context, another object of the invention is to provide an improved kit for orthopedics, preferably for osteosynthesis, which comprises a tensioning device which overcomes the drawbacks of traditional solutions and is an improvement and/or alternative to these.

Another object of the invention is to provide an improved kit for orthopedics, preferably for osteosynthesis, which includes a tensioning device which is simple, quick and easy to use, less invasive and also is vertically movable towards/ away from the outer surface of the plate.

Another object of the invention is to provide an improved kit for orthopedics, preferably for osteosynthesis, which leaves the surgeon great freedom, during the operation, on the choice of where to apply the tensioning device.

Conveniently, in the tensioning device 60 of the kit 1 according to the invention, the two members 61 and 62 are connected together by a single connecting element 63 which, preferably, is bolt-shaped (as shown in FIGS. 13, 14 and 15); however, it is intended that the two members 61 and 62 can be connected by means of an assembly of more mechanical components, assembly that is configured to approach/remove the two organs from each other, like for example these provided in a traditional turnbuckle in which there are two threaded bodies which are complementarily screwed/unscrewed within a sleeve.

Preferably, the connecting element 63, substantially configured as a bolt, comprises a rod, which is wholly or mainly threaded, and one or more head portions 64 suitably shaped so as to be engaged by suitable tools (for example a key) or knob-shaped so as to allow the operator to make the operation by hand, and this in order to rotate (and therefore screw/unscrew) the connecting element 63 with respect to an internally threaded sleeve provided in at least one of the two members 61, 62 of the tensioning device 60 and thus allow the approaching/removal of said two members 61, 62, and therefore of the corresponding bone fragments 7' and 7".

In particular, in the tensioning device 60 according to the invention at least one of said two members 61, 62 is configured to be associated with said plate 4 at the head 11 of a screw 5 which, passing through a conical through hole 8 provided in said plaque, fix the latter to a corresponding bone fragment 7' and/or 7". Preferably, at least one of said two members 61, 62 is configured to be associated with said plate 4 by means of the gripping tool 35 that engages with the female thread 41 of its tubular end portion 40 on the thread 16 of the head 11 of the screw 5 that, by passing through a conical through hole 8 provided in said plate, secures the latter to a corresponding bone fragment 7' and/or 7".

Conveniently, the first 61 and/or the second 62 member are associated—by the gripping tool 35—with the head 11 of a screw 5 which fixes the plate 4 to a bone fragment.

Advantageously, it is understood that the gripping tool 35 used in combination with the tensioning device 60 can be an instrument different and separated from the screwing tool 31, or it can comprise the adapter 42—as described above—which transforms the screwing tool 31 into said gripping tool 35.

Advantageously, the tensioning device 60 according to the invention comprises two members 61 and 62 which are connected to each other by means of the connecting element 63 which is configured to cause the mutual approach/removal of said members, and in which:

the first member 61 is configured to be associated with said plate 4 at the head 11 of a screw 5 which, passing through a conical through hole 8 provided in said plate, secures the latter to a first bone fragment 7', the second organ is configured to be fixed with a nail 69 within the other bone fragment to be joined 7".

Preferably, as mentioned, the first member 61 and the second member 62 are connected to each other by the connecting element 63. In particular, for this purpose, the first member 61 and the second member 62 have respective sleeves 65 intended to be crossed by the connecting element 63.

Suitably, the sleeve 65 of one of said members 61, 62 is internally threaded to allow engagement of the threaded portion of the connecting element 63 while the body of the other sleeve 61, 62 is internally smooth (i.e., non-threaded); however, it is understood that the sleeves of both members 61, 62 can be internally threaded or they can both be internally smooth (i.e. not threaded).

Preferably, the sleeve 65 of the first member 61 is internally smooth so that the rod (with its threaded or even non-threaded portion) of the connecting element 63 passes through this sleeve without any screwing engagement being defined, thus allowing the free sliding of the rod within this sleeve.

In addition, the first member 61 has a first tubular section 66 configured for the crossing and the guidance of the gripping tool 35. In particular, this tubular portion is destined to be positioned on the outer surface of the plate 4 in correspondence with a conical through hole 6 of the latter traversed by a fixing screw 5. More in detail, this first tubular section 66 of the first portion is dimensioned so as to house it inside the head 11 of the fixing screw 5 once the tubular end portion 40 of the gripping tool 35 has been screwed onto the head of said fixing screw 5. In substance, the diameter of the first tubular section 66 is slightly larger than the diameter of the tubular end portion 40 of the gripping tool 35 and this in order to allow a stable positioning of said portion of the instrument taken within said section.

Advantageously, the first tubular section 66 has a side opening 68 to visually check the engagement between the tubular end portion 40 of the gripping tool 35 and the head 11 of the fixing screw 5.

Conveniently, a suitable symbol 70 is also shown on the tubular end portion 40 of the gripping tool 35 to indicate the direction of rotation of the gripping tool 35 in order to cause/allow its engagement on the head 11 of the fixing screw 5.

Conveniently, in the first member 61 the sleeve 65 is integral with the first tubular section 66 and they are disposed at an angle. Preferably, in the first member 61, the axes which pass respectively through the sleeve 65 and the first tubular section 66 are arranged in a substantially perpendicular manner to each other.

Preferably, the sleeve 65 and the first tubular section 66 of the first member 61 are obtained from a single piece or can be made in two distinct pieces rigidly coupled (e.g. by welding) to each other.

The second member 62 includes a second tubular section 67 configured for crossing and the guidance of a nail 69 destined to be inserted in a corresponding cavity formed in one of the fragments of a bone.

Suitably, the second member 62 the sleeve 65 is integral with the second tubular section 67 and, preferably, are disposed at an angle between them. Preferably, in the second member 62, the axes which pass respectively through the sleeve 65 and the second tubular section 67 are arranged in a substantially perpendicular or slightly angled manner to each other; appropriately, in this way, the angle defined between the connecting element 63 and the nail 69 can be substantially equal to or even lower than 90°.

Preferably, the sleeve 65 and the second tubular section 67 of the second member 62 are formed in a single piece or can be formed in two distinct pieces made integral (for example by welding) between them.

Conveniently, by sliding the tubular sections 66 and 67, of the first and second member 61 and 62 respectively, along the stem of the gripping tool 35 and along the nail 69 respectively it is possible to move away the tensioning device 60 (comprising said members 61 and 62 with the connecting element 63) with respect to the upper surface of the plate 4, thus allowing access to the bone fragments even when around these other tissues, such as muscles or ligaments to be preserved are present. Conveniently, in the section of the connecting element 63 interposed between the two members 61 and 62 a tightening nut (not shown) may be provided on which to act to separate said organs, and therefore the respective bone fragments, from each other; acting instead at the head portion 64, the two members 61 and 62 and therefore of the corresponding bone fragments 7', 7" are brought closer together.

The use of the tensioning device 60 to cause the compression of two bone segments 7', 7" at their contact area 59 is the following:

the plate 4 is placed on either side of the contact area 59 of the bone fragments 7' and 7" to be joined;

a first end portion of the plate 4 is fixed to a first bone fragment 7' by inserting at least one fixing screw 5 into respective conical through holes 8 provided in the plate itself, the other extremal portion of the plate 4 of the tip centering device 50 is inserted in correspondence with the conical through holes 8 of the plate itself, the gripping tool 35 is inserted within the first tubular section 66 of the first member 61 of the tensioning device 60 and the gripping tool 35 is screwed so that its tubular end portion 40 engages on the head 11 of the fixing screw 5 associated with the first extremal portion of the plate 4; advantageously, in the case of using the adapter 42, the engagement of the gripping tool 35 on the head 11 of the fixing screw 5 is facilitated by the presence of the screwing tool 31 which, crossing the tubular stem 38 of the adapter, is inserted into the recessed mark 15 provided in the head 11 of said screw 5, the nail 69 is inserted within the second tubular section 67 of the second member 62 of the tensioning device 60 and is fixed within the second bone fragment 7″; at this point, the tensioning device 60 is applied by means of its members 61, 62 (connected to each other by means of the connecting element 63) to the two bone fragments 7′ and 7″ to be joined and compressed together at the area of mutual contact 59, the connecting element 63 is rotated, preferably by acting on its head portion 64, so as to cause the two members 61 and 62 to come closer together, and thus the corresponding bone fragments 7′, 7″ to which said members are associated, so as to compress said bone fragments together at their contact area 59; suitably, the top of the connecting element 63 rotation is done manually, and thereafter rotated by means of a suitable tool (such as a screwdriver which engages within the hollow provided in the portion of a head portion 64 of the connecting element 63, which can act as a lever as well, or by means of a key), the corresponding longitudinal cavities 52 are formed on the second bone fragment 7″ by inserting a drilling tip 51, or another drill bit, within the tip centering device 50 previously coupled into corresponding conical through holes 8 of the other end portion of the plate 4;

after removing the tip centering devices 50 from the conical through holes 8, the fixing screws 5 are then inserted—according to the methods described above and by means of the screwing tool 31—inside the aforesaid longitudinal cavities 52 which are aligned with said holes, to attach the plate 4 also to the second bone fragment 7″ and thus keep the condition of compression achieved and obtained through the use of the tensioning device 60.

From the aforegoing it is apparent that the kit according to the invention is particularly advantageous in that:

it is of simple and rapid production, and therefore of low costs, it is ready, quick and easy to use, both for the installation phase of the system and for removal, it allows an easy cleaning of a plate that has been positioned in the area to be treated but without having been implanted, thus allowing its reuse, it also includes a tensioning device which is minimally invasive and is simple, quick and easy to use.

The invention claimed is:

1. A kit for orthopedics, comprising:
a mechanical fixing system, which includes a plate to be mounted straddling two bone fragments to be joined, and fixing screws for fixing the plate to said two bone fragments;
wherein said plate is made of a biocompatible metal material and has a thickness of about 0.5-4 mm, said plate being provided with conical through holes each having an inner wall obtained with at least one surface finishing mechanical operation,
wherein each of said fixing screws has a head and a self-tapping stem,
wherein each of said fixing screws comprises a conical collar, which is interposed between said head and said self-tapping stem, and which is configured to define a conical coupling within a corresponding conical through hole of the plate, the head presenting, on an upper surface thereof, a recessed mark for shape coupling, at least partially, with a tip of a screwing tool, said head further presenting, on an external side wall thereof, a thread for the engagement of a gripping tool,
wherein each of said fixing screws is configured so that, when the conical collar is inserted into the corresponding conical through hole of the plate, said head protrudes outwards with respect to said plate for allowing the engaging of said gripping tool on said head, and
wherein each of said fixing screws comprises a flange connecting the head to the conical collar, said flange being configured to be spaced with respect to an outer surface of the plate when the conical collar is inserted within the corresponding conical through hole of the plate.

2. The kit according to claim 1, wherein said recessed mark of the head of said fixing screws is shaped as a six-pointed star.

3. The kit according to claim 1, wherein said recessed mark of the head of said fixing screws has a hollow central portion surrounded by lateral discharge grooves, which are not provided in a corresponding full shape defined by the tip of the screwing tool.

4. The kit according to claim 1, wherein the inner wall of each conical through hole of the plate is inclined about 1-2° with respect to an axis passing through the through hole.

5. The kit according to claim 1, wherein each through hole is obtained by performing in sequence:
a drilling operation for obtaining a cylindrical hole which passes through an entire thickness of the plate,
a reaming operation to produce a conical-shaped hole from the cylindrical hole previously made, and
a rolling operation on the inner wall of the conical-shaped hole previously obtained.

6. The kit according to claim 1, further comprising the screwing tool, which is provided with:
a handle to be gripped by an operator, and
a stem, which is associated with said handle and which has the tip with a full shaped portion so as to be engaged by the shape coupling of the shape of the recessed mark on the upper surface of the head of one of the fixing screws, so that, once engaged, a rotation of said tip drags said one of the fixing screws into rotation.

7. The kit according to claim 6, further comprising an adapter configured to transform the screwing tool into the gripping tool, said adapter including a tubular stem, internally hollow, inside which the stem of the screwing tool is to be inserted, said tubular stem having a tubular end portion which is internally hollow and which is internally provided with a female thread configured for screwing to the thread provided on the external side wall of the head of the fixing screw.

8. The kit according to claim 1, further comprising the gripping tool which is provided with a stem which has a tubular end portion that is internally hollow and is internally provided with a female thread adapted to be screwed to the thread provided on the external side wall of the head of the fixing screws.

9. The kit according to claim 1, further comprising a tensioning device, which comprises two members, to be associated with the two bone fragments, and which are connected to each other so as to allow their mutual approach/removal, at least one of said two members being configured to be associated to said plate by said gripping tool which passes through and/or is associated with one of said members and which is screwed with a tubular end portion of the gripping tool onto the thread of the head of one of the fixing screws which, passing through one of the conical through holes provided in said plate, fix the plate to a corresponding bone fragment.

10. The kit according to claim 1, further comprising a tip centering device which is configured to guide a drilling tip so as to create a longitudinal cavity in one of the two bone fragments, inside which one of the fixing screws, which is aligned with an axis that passes through one of the conical through holes of the plate, is intended to be inserted and housed, said tip centering device comprising a tubular element with an internal channel which is configured to be crossed by and for guiding said drilling tip, said tubular element presenting:

- an end portion, which is conical and is shaped to engage within a corresponding conical through hole of the plate so that said internal channel is aligned with the axis that passes through said corresponding conical through hole, and
- at another end portion, an inlet portion of said internal channel, which has a greater cross-section than a remaining, inner part, of said channel.

* * * * *